United States Patent [19]

Bennett, deceased

[11] Patent Number: Plant 7,449

[45] Date of Patent: Feb. 19, 1991

[54] MINIATURE ROSE NAMED 'TEENY BOPPER'

[75] Inventor: Cecilia L. D. Bennett, deceased, late of Chula Vista, Calif., by Susan M. O'Brien, administrator

[73] Assignee: Susan O'Brien, Chula Vista, Calif.

[21] Appl. No.: 460,231

[22] Filed: Jan. 2, 1990

[51] Int. Cl.[5] ..... A01H 5/00

[52] U.S. Cl. ..... Plt./7

[58] Field of Search ..... Plt./7, 9, 10

*Primary Examiner*—James R. Feyrer

[57] ABSTRACT

The subject of the present invention disclosure is a new and distinct variety of miniature rose plant, named 'Teeny Bopper', which is characterized by its small blooms of near White with petal margins ranging from near Carmine to near Cardinal Red to near Chrysanthemum Crimson. The blooms are usually borne one to a stem with hybrid tea form but on occasion may be produced in sprays of 3 to 5 or more. The bush is compact, well-branched and produces moderate to heavy quantity of blooms. (More detailed description to follow.)

1 Drawing Sheet

The present invention relates to a new and distinct variety of a hardy, dwarf, bush plant of the miniature class; the variety being primarily characterized as red blend.

The variety is further characterized by:

Small bloom of hybrid tea-type form, borne usually one to a stem but on occasion in sprays of 3 to 5 or more. The blooms are held erect and well above the foliage.

The plant ranges in height from 8 to 12 inches (20 to 30 cm). The canes are sturdy and erect with moderate to heavy branching and foliage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The self-pollenated seed parent was Little Squirt (miniature; deep yellow; Cecilia Bennett; introduced by the Tiny Petals Nursery; 1983). It differs from its parent in the following ways. It produces red blend blooms with hybrid tea form, and Little Squirt produces yellow blooms with fewer petals and decorative form.

The single color photographic view shows, in plan view, a bouquet of 'Teeny Bopper' in various stages of maturity from bud to full blown stage.

The descriptive matter which follows pertains to roses grown and color values observed in plants and newly opened blooms in the months of March through November 1989. The plants were grown outdoor in Chula Vista, Calif., and are believed to be accurate standards for this cultivar in similar conditions of soil and climate elsewhere.

Referring now specifically to the new and distinct variety of miniature rose plant named 'Teeny Bopper', the following is a detailed description thereof in outline; all major color plate identications being by reference to the British Colour Council Horticultural Chart, except where common terms of color definition are employed.

Type: Hardy, dwarf, bushy, greenhouse or outdoor, exhibition or garden decorative potted plant.

Class: Miniature.

Variety name: Teeny Bopper.

Flowers Borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Short length (15 to 25 mm); average diameter and sturdy; ranging from near Scheele Green (860/3 to 860/1 page 176) with occasional tinting of bronze.

*Hairs.*—Few if any, extremely small and reddish in color; located over the surface of the peduncle.

*Calyx.*—Color range same as peduncle.

*Opening.*—Opens well in all weather.

Bloom:

*Size when fully open.*—Small for a miniature variety (15 to 20 mm).

*Petalage.*—Double — 20 to 25 petals, arranged regularly, plus 5 to 7 petaloids.

*Form.*—Urn-shaped to ovoid as the bloom progresses. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer petals are of a broad obovate form with a peak at the apex. The intermediate petals are very much like the outer petals only narrower. The inner petals are a broad lanceolate form; and the petaloids are also lanceolate with some occasional irregularities.

Color: Newly opened flowers from plants grown outdoors (March throug November of 1989), Chula Vista, Calif.:

*Outer Petals.*—Upper and under surfaces — Ranging from near Cardinal Red (822/2 to 822 page 168) to near Chrysanthemum Crimson (824/3 to 824/1 page 169) with a base of near White.

*Intermediate/middle petals.*—Upper and under surfaces — Ranging from near Carmine (21/3 to 21/1 page 21) to near Cardinal Red (822/3 to 822/1 page 168) at the margins with the body of the petals near white.

*Inner petals.*—Upper and under surfaces — Near white with a slight edge of near Carmine (21/3 to 21/2 page 21).

*General color effect.*—Newly opened flowers — Near white at the middle with margins and outer petals in tone of red. Three days open — All petal surface which have been exposed to sunlight are blending to tone of red. Three to five days open — All sun-exposed surfaces are red with some near white evident only where petals have reflexed, revealing lower petal surfaces previously unexposed to sunlight. Photosensitive response is not evident on blooms opened indoors; only sun-exposed surfaces will turn red, and all other area will remain near white as bloom opens.

*Flower longevity.*—(March through November 1989) Plant in pot 3 to 5 days from bud with sepals reflexed to fully open bloom. Holding at fully opened with increased red tones on all petals exposed to sunlight for 3 to 5 days longer. Cut blooms at living room temperature 5 to 7 days or longer with no color change evident, except on petal surfaces exposed to sunlight.

Reproductive organs:

*Stamens.*—A generous amount arranged uniformly around the pistill.

*Filaments.*—Varing in length with shorter filaments more proximal to the pistil; pale yellow in color with anthers of golden yellow.

*Pollen.*—Abundant.

*Pistil.*—Short, spreading and abundant; pale yellow to pale green.

*Ovaries.*—All encased in calyx.

*Hips.*—Some.

*Seeds.*—3 to 5 or more in each hip.

*Sepals.*—Permanent; spear-shaped; open as the bloom opens, recurving against the peduncle, when the bloom is fully opened.

Foliage:

*Leaves.*—Five to seven leaflets on the average; small size for a miniature rose plant.

*Leaflets.*—Broad ovate-shaped.

*Margins.*—Very serrated with tinting of bronze, especially noticeable on the newer foliage.

*Color.*—Ranging from near Scheeles Green (860/2 to 860 page 175) to near Spinach Green (0960/2 to 0960/1 page 0960) with bronzing of the margins. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 very small thorns.

*Stipules.*—Varying in length from very small to medium; average width; tapering auricles angled outward at about 45 degrees.

Growth:

*Habit.*—Dwarf, bushy; small for a miniature rose plant.

*Growth.*—Compact and well-branched.

*Canes.*—Medium diameter; sturdy; held erect.

*Main stems.*—Color range same as foliage.

*Thorns.*—None on the stems or canes.

*Branches.*—Color range same as foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named, 'Teeny Bopper' of hardy, dwarf, compact growth, well-branched and attractive in appearance, substantially as illustrated and described, characterized by its hybrid tea form blooms in near white with margins, ranging from near Cardinal Red to near Chrysanthemum Crimson to near Carmine, with flowers borne usually one to a stem but occasionally in sprays of 3 to 5 or more.

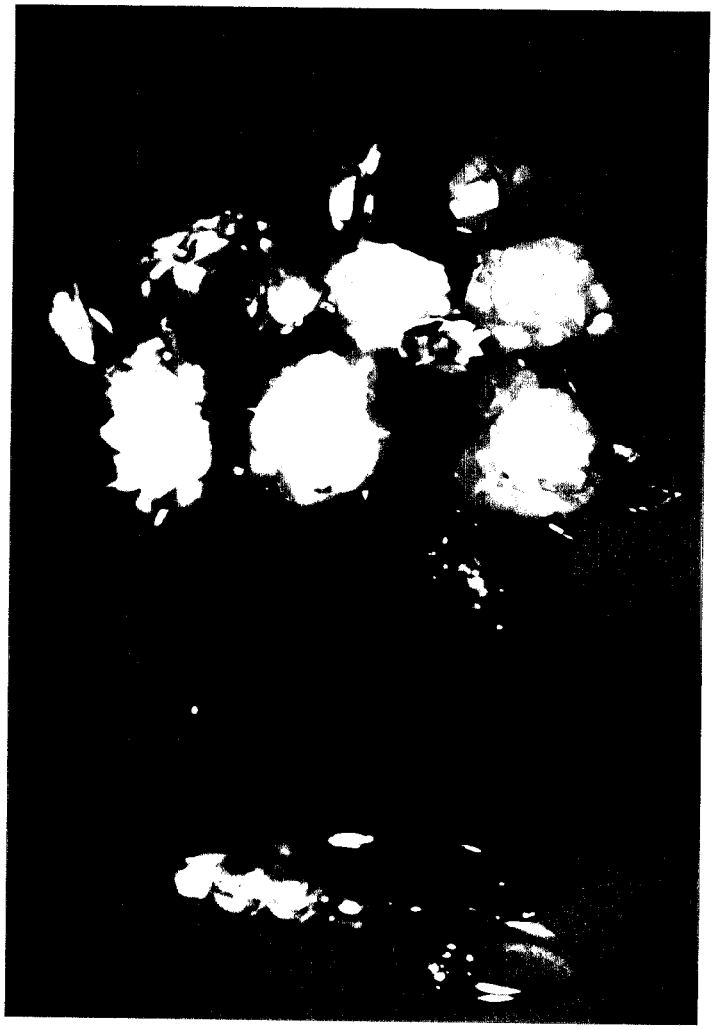

* * * * *